(12) United States Patent
Watson et al.

(10) Patent No.: US 8,193,823 B2
(45) Date of Patent: Jun. 5, 2012

(54) ASSEMBLY FOR ELECTRICAL CONDUCTIVITY MEASUREMENTS IN THE PISTON CYLINDER DEVICE

(75) Inventors: Heather Christine Watson, Dublin, CA (US); Jeffrey James Roberts, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 499 days.

(21) Appl. No.: 12/428,559

(22) Filed: Apr. 23, 2009

(65) Prior Publication Data

US 2010/0271055 A1 Oct. 28, 2010

(51) Int. Cl.
*G01R 27/08* (2006.01)
*G01R 27/00* (2006.01)

(52) U.S. Cl. ............................ 324/722; 324/691; 702/65

(58) Field of Classification Search .................. 324/722, 324/691, 649, 600, 378; 702/57, 64, 65, 702/1
See application file for complete search history.

(56) References Cited

U.S. PATENT DOCUMENTS

| 294,124 A | 6/1960 | Hall |
| 294,125 A | 6/1960 | Hall |
| 294,428 A | 7/1960 | Hall |
| 5,272,417 A * | 12/1993 | Ohmi ........................ 315/111.21 |
| 6,824,813 B1 * | 11/2004 | Lill et al. ........................... 427/8 |
| 2007/0196011 A1* | 8/2007 | Cox et al. ....................... 382/145 |
| 2007/0268027 A1* | 11/2007 | Olsen et al. .................... 324/691 |
| 2008/0084650 A1* | 4/2008 | Balasubramanian et al. 361/234 |

OTHER PUBLICATIONS

F.R.Boyd et al, "Apparatus for Phase-Equilibrium Measurements at Pressures up to 50 Kilobars and Temperatures up to 1750° C", Journal of Gephysical Research, Feb. 1960 p.

* cited by examiner

*Primary Examiner* — Hoai-An D Nguyen
(74) *Attorney, Agent, or Firm* — Eddie E. Scott

(57) ABSTRACT

An assembly apparatus for measurement of electrical conductivity or other properties of a sample in a piston cylinder device wherein pressure and heat are applied to the sample by the piston cylinder device. The assembly apparatus includes a body, a first electrode in the body, the first electrode operatively connected to the sample, a first electrical conductor connected to the first electrode, a washer constructed of a hard conducting material, the washer surrounding the first electrical conductor in the body, a second electrode in the body, the second electrode operatively connected to the sample, and a second electrical conductor connected to the second electrode.

19 Claims, 4 Drawing Sheets

ASSEMBLY FOR ELECTRICAL CONDUCTIVITY MEASUREMENTS IN THE PISTON CYLINDER DEVICE

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to the piston cylinder device and more particularly to an assembly for electrical conductivity and other measurements in the piston cylinder device.

2. State of Technology

The piston cylinder device is closely related to the device described in the article "Apparatus for Phase-Equilibrium Measurements at Pressures up to 50 Kilobars and Temperatures up to 1750° C." by F. R. Boyd and J. L. England in the Journal of Geophysical Research, Volume 65, No. 2, pp 741, February 1960. These types of high-pressure apparatuses can be fitted with a resistance heater, typically a sample-surrounding cylinder of graphite or another electrically conducting heating element, for studies at temperatures up to 2,000° C."

U.S. Pat. No. 2,941,248 describes the piston cylinder device as quoted below. U.S. Pat. No. 2,941,248 is incorporated herein by this reference in its entirety for all purposes.

"An apparatus capable of producing temperatures of the order of several thousand degrees Centigrade and pressures of the order of 40,000 to 100,000 atmospheres for sustained time intervals is desirable to effect and control reactions occurring under such conditions. The reactions of various specimen materials subjected to such high pressures and high temperatures may be employed for research study purposes or to obtain physical and chemical changes which give added characteristics to given materials. An example of such a process of reaction is the transformation of carbonaceous materials to diamond under high pressures and temperatures. Pressures of the above order may cause explosive rupture of prior high pressure apparatus at TOOM temperature, while tendency to rupture would be increased if the high pressure device were subjected also to temperatures of the mentioned range."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an assembly apparatus for measurement of electrical conductivity and/or other properties of a sample in a piston cylinder device. The piston cylinder device is defined in the Encyclopedia Britannica as:

"The piston-in-cylinder design, in use for more than a century, incorporates a strong metal or carbide piston that is rammed into a sample-confining cylinder. In principle, the piston can be quite long, so a piston-cylinder design can accommodate a much larger volume of sample than the squeezer, depending on the dimensions of the sample-holding cylinder. These devices are rarely used at pressures above about 10 GPa owing to the likelihood of lateral failure (namely, explosive bursting) of the metal cylinder.

The present invention provides an assembly apparatus for electrical conductivity and other measurements in the piston cylinder device wherein pressure and heat are applied to the sample by the piston cylinder device. As used in this application the term "piston cylinder device" means: a device that includes a piston that is driven into a sample confined in a cylinder. The device includes a heating unit for heating the sample and a processor for measuring electrical conductivity or other properties of the sample.

The assembly apparatus includes a body, a first electrode in the body, the first electrode operatively connected to the sample, a first electrical conductor connected to the first electrode, a washer constructed of a hard material, the washer surrounding the first electrical conductor in the body, a second electrode in the body, the second electrode operatively connected to the sample, and a second electrical conductor connected to the second electrode.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
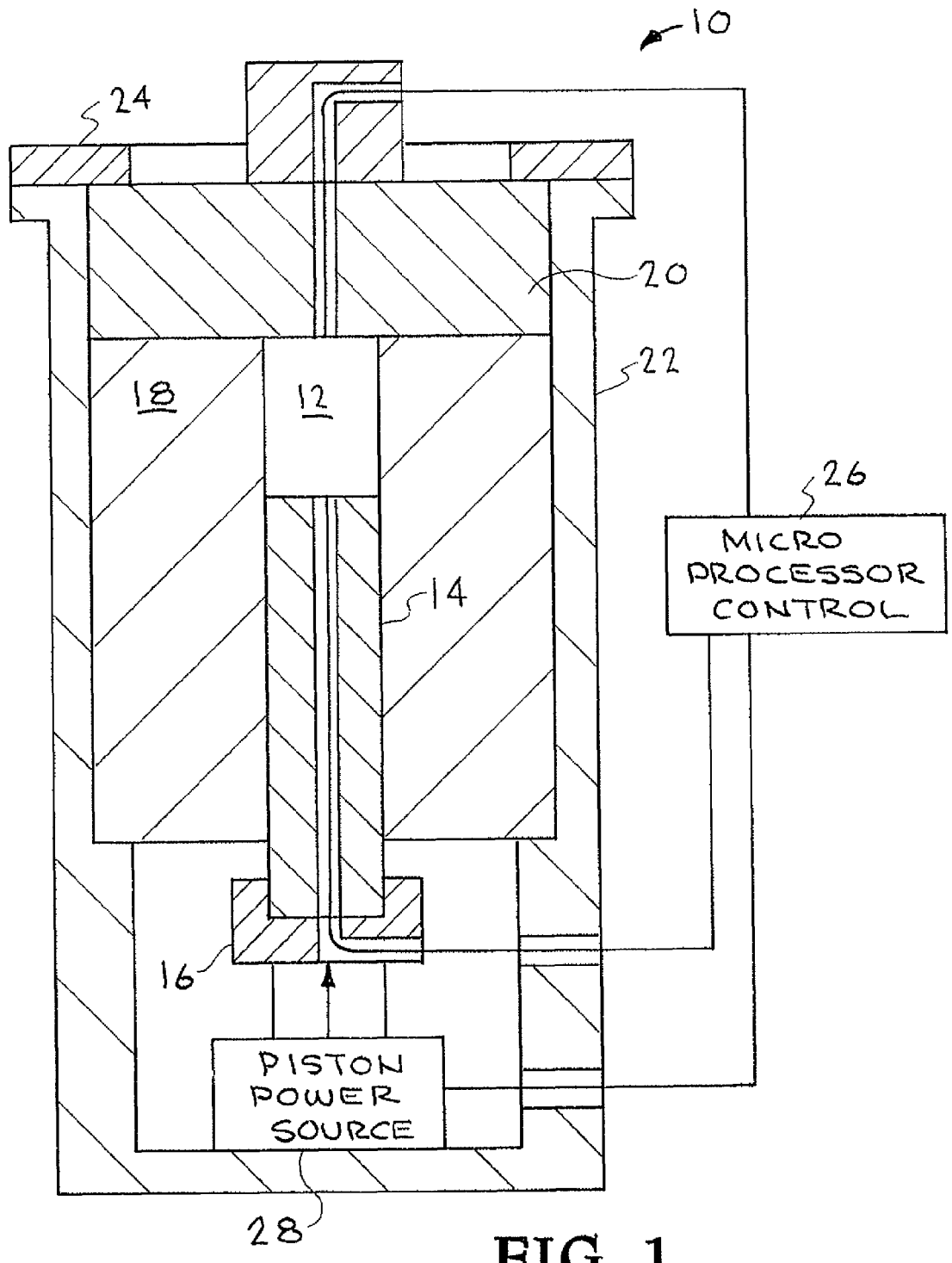
FIG. 1 is a cross sectional view of the piston cylinder device.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, a cross sectional view of the piston cylinder device is shown. The piston cylinder device is designated generally by the reference numeral 10. The piston cylinder device 10 includes the following components. An assembly apparatus for electrical conductivity measurements in the piston cylinder device is designated generally by the reference numeral 12. The assembly apparatus 12 for electrical conductivity measurements in the piston cylinder device will be shown in detail in FIG. 2 and will be described in greater detail subsequently. The assembly apparatus 12 is surrounded by casing 18. A piston 14 abuts the lower end of assembly apparatus 12. The piston 14 rests in piston seat 16. The piston 14 and seat 16 are in contact with a piston power source 28. The piston power source 28 moves the piston 14 upward compressing the assembly apparatus 12 which is in contact with anvil 20. Passages for electrical conductors are shown allowing electrical leads to connect to micro-processor control 26. The leads from assembly apparatus 12 will be shown and described in greater detail in FIG. 2. The above described items are enclosed in housing 22 and cover plate 24.

The assembly apparatus is an assembly for the end-loaded piston cylinder device in which electrical conductivity can be measured. The assembly apparatus includes a cylindrical sample, which can be single crystal or polycrystalline. On either side of the sample are disk-shaped electrodes consisting of metal. Contact for electrical measurements is made by separate wires exiting the sample through the top and bottom that physically touch the electrodes. A notable feature of this design is the bottom piston that has a hole that accommodates an alumina tube and the electrical lead. The sample is surrounded by alumina, magnesia, or other insulating ceramic. A metallic electrical shield is used between the graphite furnace and the insulated sample assembly to minimize noise caused by the AC powered furnace. Factors in the design are the size (length) of the four-hole alumina tubes used to insulate the electrical leads and the Ni washer that protects the alumina tube at the bottom of the sample assembly. The length must be correct to prevent shearing of the leads and shorting of the lead to the metallic body of the PC apparatus and penetration into and disruption of the sample, while the washer prevents intrusion of softer ceramic or graphite from the heater into the end of the tube causing electrical shorts.

Figure 2:
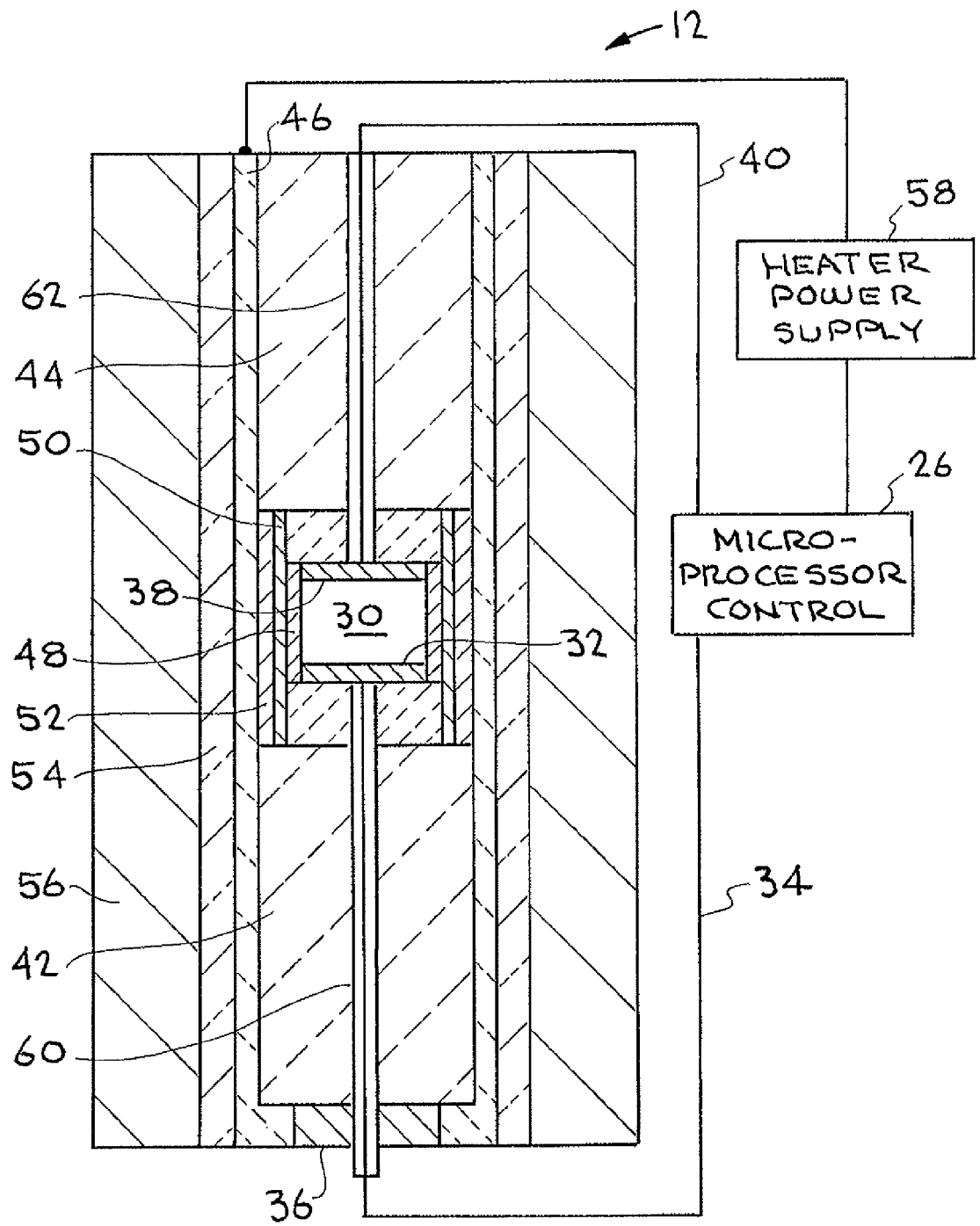
FIG. 2 illustrates an embodiment of the assembly apparatus for electrical conductivity measurements in the piston cylinder device.

Referring now to FIG. 2, an embodiment of the assembly apparatus for electrical conductivity measurements in the piston cylinder device is illustrated. This embodiment is designated generally by the reference numeral 12. The assembly apparatus 12 includes a body with a first electrode 32 in the body. The first electrode 32 is operatively connected to the sample 30. A first electrical conductor 34 is connected to the first electrode 32. A washer 36 is constructed of a hard metallic material. The washer 36 is positioned surrounding the first electrical conductor 34 in the body. A second electrode 38 is operatively connected to the sample 30. The second electrode 38 operatively connected to the sample. A second electrical conductor 40 is connected to the second electrode 38.

The sample unit 12 is shown greatly enlarged for purposes of illustration in FIG. 2. The sample to be tested 30 is in contact with the first electrode 32 and the second electrode 38. The first electrode 32 connects to the conductor 34 that is encased in a rigid ceramic tube 60. The conductor 34 connects to a micro-processor 26. The second electrode 38 connects to the second conductor 40. The second conductor is encased in a rigid ceramic tube 62. Conductor 40 connects to the micro-processor 26. The rigid ceramic tubes 60 and 62 both electrical insulate and physically protect the conductors 34 and 40.

The sample 30 is surrounded by VYCOR ring 48. The VYCOR ring 48 is in contact with a magnesia ceramic ring surrounded by an electrical shield ring 50. Shield ring 50 is a metallic foil and it's purpose is to minimize noise caused by the AC powered furnace 46. A fired phrophyllite ring 52 resides between foil metallic shield ring 50 and the graphite heater element 46. Additional elements of sample unit 12 are pyrex cylinder 54 and salt casing cylinder 56 and magnesium oxide inserts 42 and 44. An important component of the assembly apparatus 12 is the rigid washer 36. The rigid washer 36 will be described greater detail in FIGS. 3A and 3B.

The assembly apparatus 12 provides reliable and reproducible measurement of electrical conductivity in the piston cylinder device. The assembly apparatus 12 permits the measurement of frequency-dependent (AC) electrical properties at temperatures up to 1400 C and pressures up to 1.5 GPa.

The assembly apparatus 12 combined with the piston-cylinder device can be used for monitoring and determining the state and physical properties of materials during high pressure, high temperature experiments. Properties that can be determined include the physical state of the sample (solid, liquid, or partially-molten), electrical conductivity, diffusivity of specific ions and defects, grain growth, phase stability. The assembly 12 addresses several technical problems needed to be overcome for the routine measurement of electrical conductivity in the piston-cylinder (PC) apparatus. These include: (1) Transmittal of pressure to the sample, (2) Electrical shielding of the sample from thermocouple and furnace noise, (3) Sample stability, (4) Electrode contact, (5) Sample shape and orientation, and (6) Maintaining the sample in electrical isolation. Prior designs have addressed some of the issues independently. The assembly 12 accomplishes all required aspects simultaneously. Prior designs have had limited success in performing reliable measurements on a routine basis.

Figure 3A:
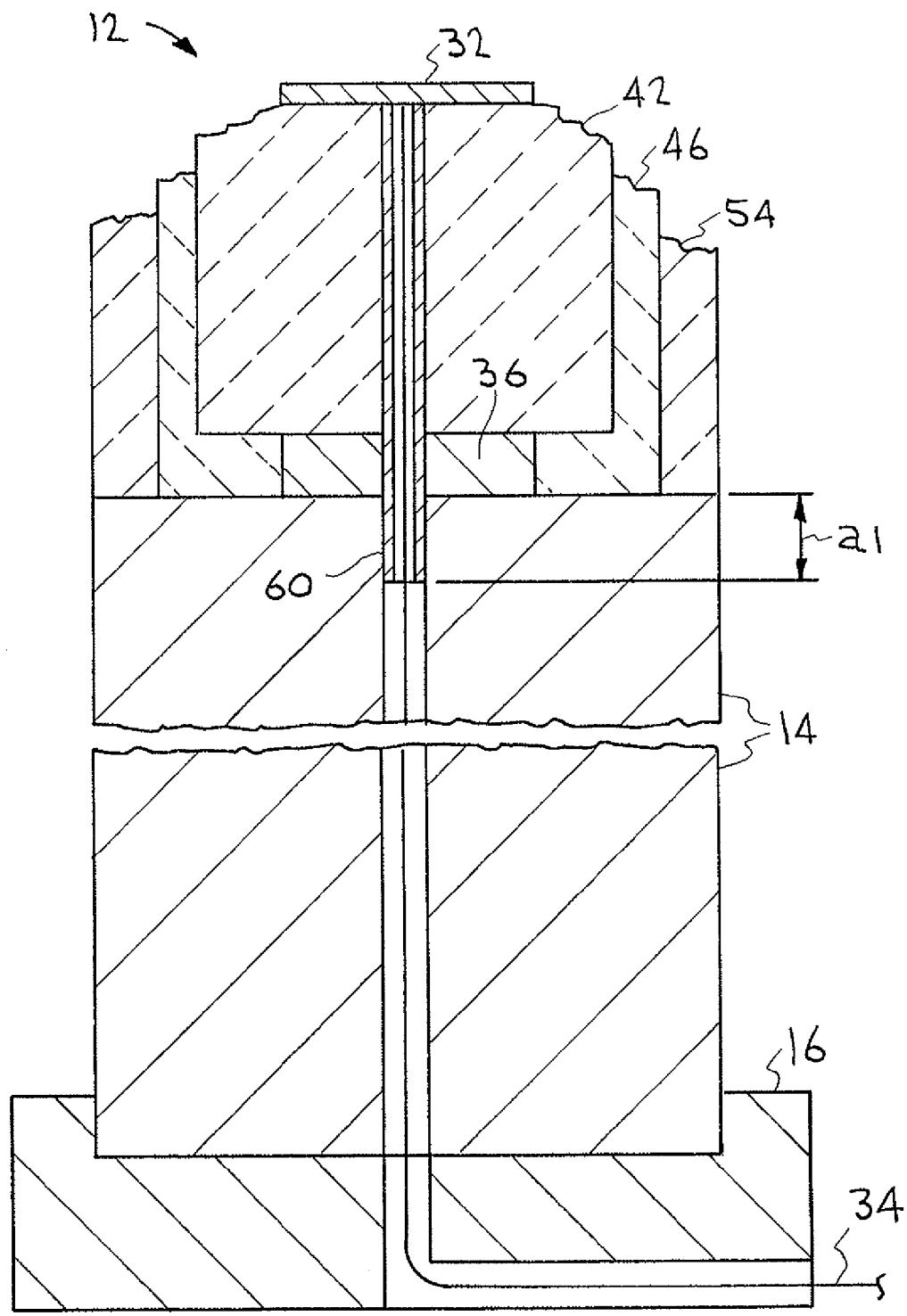
FIGS. 3A and 3B illustrated the rigid washer in greater detail.
Figure 3B:
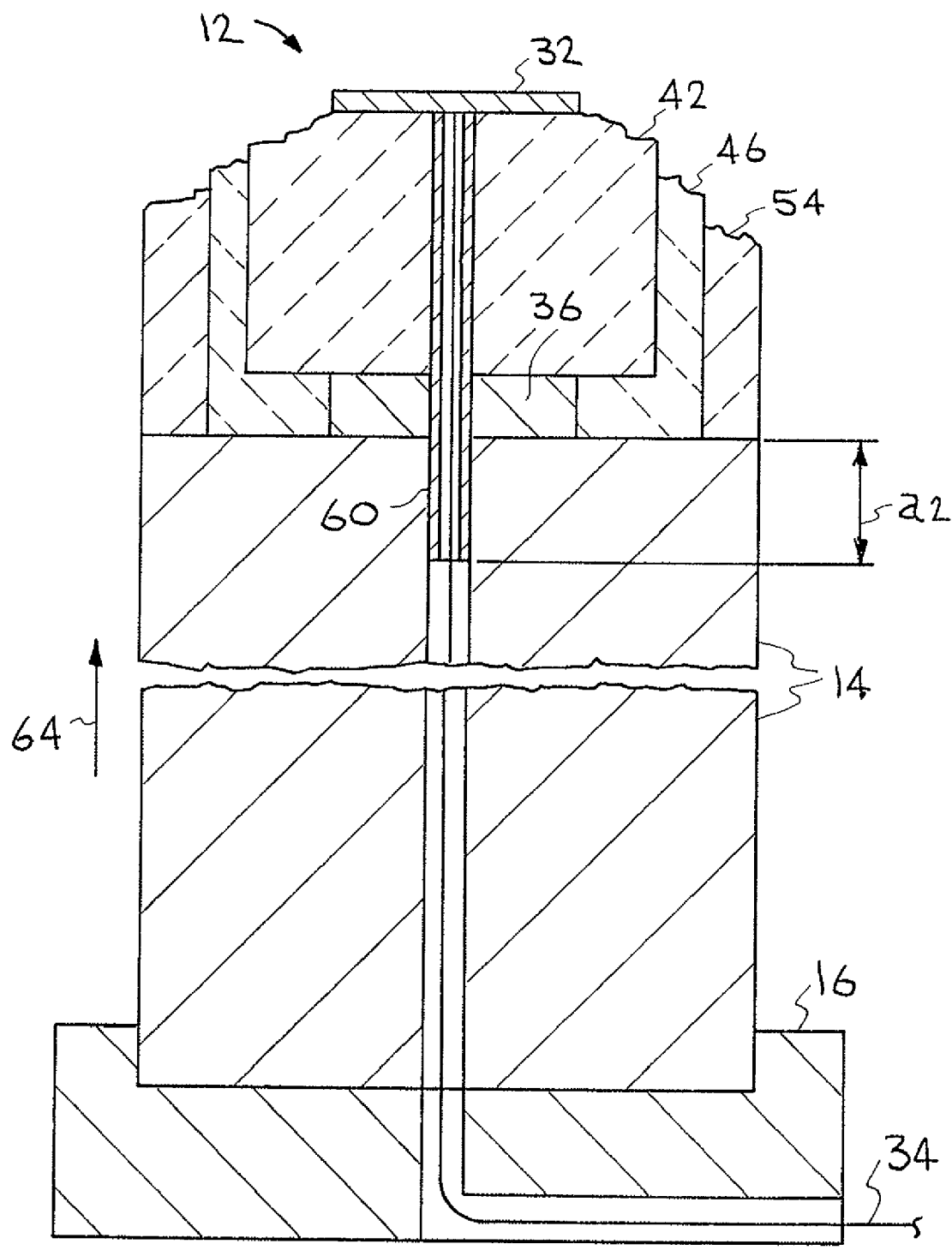

Referring now to FIGS. 3A and 3B, the rigid washer 36 is described greater detail. The washer 36 is constructed of a hard material. As used in this application the term "hard material" means: dynamic hardness and means a material that is hard, strong, durable, and resistant to deformation. Examples of a "hard material" washer include a washer made of nickel, iron, titanium, or aluminum or alloys of nickel, iron, titanium, and/or aluminum.

FIGS. 3A and 3B are both partial sectional views of the piston 14 and the sample unit 12. In FIG. 3A the unit is at rest and for illustrative purposes the dimensional shows the rigid ceramic tube 60 projecting a distance a1 into the piston. In FIG. 3B the piston 14 is applying a force on the assembly apparatus 12 in the direction of arrow 64. As force is applied to assembly apparatus 12 the less rigid materials 42, 46, 54 of assembly apparatus 12 will deform. The rigid ceramic tube will now project further into the piston 14 as indicated by dimension a2. If the rigid washer 36 was not present to support the ceramic tube 60 the deformation of the aforementioned materials would cause the ceramic tube to fail, compromising the conductor 34. The assembly apparatus 12 has been built and tested and provides improved and unexpected results compared to apparatus of the prior art.

The present invention provides a method of measuring electrical conductivity or other properties of a sample. The method includes the steps described below. A measurement assembly body is provided that is made of alumina, magnesia, or other insulating ceramic or combinations of alumina, magnesia, or other insulating ceramic. A first electrode is positioned in the measurement assembly body and is operatively connected to the sample. A first electrical conductor is connected to the first electrode. A washer constructed of hard metal is positioned surrounding the first electrical conductor in the measurement assembly body. A second electrode is positioned in the measurement assembly body operatively connected to the sample. A second electrical conductor is connected to the second electrode. The sample is positioned in the measurement assembly. The measurement assembly is positioned in a piston cylinder device. Pressure is applied to the sample using the piston cylinder device. The sample is heated using the piston cylinder device and electrical conductivity or other properties of the sample are measured. In one embodiment, an electrical shield is positioned surrounding the sample, the first electrode, and the second electrode. In another embodiment a first alumina tube is positioned in the measurement assembly body with the first alumina tube containing the first electrical conductor. In another embodiment a second alumina tube is positioned in the measurement assembly body with the second alumina tube containing the second electrical conductor.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for measurement of electrical conductivity or other properties of a sample, comprising:
   a casing,
   a piston in said casing,
   a sample location in said casing,
   a first electrode in said body, said first electrode operatively connected to said sample location and the sample,
   a ceramic tube,
   a first electrical conductor in said ceramic tube and connected to said first electrode,
   a washer constructed of a hard conducting material, said washer having a central opening with said ceramic tube and first electrical conductor located in said central opening with said washer surrounding said first electrical conductor in said body,
   a second electrode in said body, said second electrode operatively connected to the sample, and
   a second electrical conductor connected to said second electrode.

2. The apparatus of claim 1 wherein said washer is a washer constructed of a material that is hard, strong, durable, and resistant to deformation.

3. The apparatus of claim 1 wherein said washer is a hard metal washer.

4. The apparatus of claim 1 wherein said washer is a hard metal washer constructed of nickel, iron, titanium, or aluminum.

5. The apparatus of claim 1 wherein said washer is a hard metal washer constructed of nickel.

6. The apparatus of claim 1 wherein the sample has a first side and a second side and wherein said first electrode contacts said first side of the sample and said second electrode contacts said second side of the sample.

7. The apparatus of claim 1 including a microprocessor, wherein said first electrical conductor and said second electrical conductor are connected to said microprocessor.

8. The apparatus of claim 1 including an electrical shield surrounding the sample, first electrode, and said second electrode.

9. The apparatus of claim 1 wherein said casing is made of alumina, magnesia, or other insulating ceramic or combinations of said alumina, magnesia, or other insulating ceramic.

10. An apparatus for measurement of electrical conductivity or other properties of a sample wherein pressure and heat are applied to the sample, comprising:
    a casing, said casing made of alumina, magnesia, or other insulating ceramic or combinations of said alumina, magnesia, or other insulating ceramic;
    a piston in said casing;
    a first electrode in said body, said first electrode being a disk-shaped metal electrode operatively connected to the sample;
    a first electrical conductor connected to said first electrode,
    a ceramic tube in said casing, said ceramic tube containing said first electrical conductor;
    a washer constructed of hard conducting metal, said washer having a central opening with said ceramic tube and first electrical conductor located in said central opening wherein said washer surrounds said ceramic tube and first electrical conductor in said casing;
    a second electrode in said body said second electrode operatively connected to the sample, and
    a second electrical conductor connected to said.

11. The apparatus of claim 10 including an electrical shield surrounding the sample, said first electrode, and said second electrode.

12. The apparatus of claim 10 including a microprocessor, wherein said first electrical conductor and said second electrical conductor are connected to said microprocessor.

13. The apparatus of claim 10 wherein said washer is a washer constructed of a material that is hard, strong, durable, and resistant to deformation.

14. The apparatus of claim 10 wherein said washer is a hard metal washer.

15. The apparatus of claim 10 wherein said washer is a hard metal washer constructed of nickel, iron, titanium, or aluminum.

16. The apparatus of claim 10 wherein said washer is a hard metal washer constructed of nickel.

17. The apparatus of claim 10 wherein the sample has a first side and a second side and wherein said first electrode contacts said first side of the sample and said second electrode contacts said second side of the sample.

18. A method of measuring electrical conductivity or other properties of a sample, comprising the steps of:
    providing a measurement assembly including providing a measurement assembly body made of alumina, magnesia, or other insulating ceramic or combinations of said alumina, magnesia, or other insulating ceramic, said assembly including a casing and a piston within said casing;
    positioning a first electrode in said measurement assembly body operatively connected to the sample;
    positioning a ceramic tube in said measurement assembly body;
    connecting a first electrical conductor to said first electrode;
    positioning said first electrical conductor in said ceramic tube;
    positioning a washer constructed of hard metal surrounding said ceramic tube and said first electrical conductor in said ceramic tube in said measurement assembly body;

positioning a second electrode in said measurement assembly body operatively connected to the sample;
connecting second electrical conductor connected to said second electrode;
positioning the sample in said measurement assembly;
applying pressure to the sample using said piston;
applying heat to the sample using said piston; and
measuring electrical conductivity or other properties of the sample.

19. The method of measuring electrical conductivity or other properties of a sample of claim 18 including positioning an electrical shield surrounding the sample, said first electrode, and said second electrode.

* * * * *